United States Patent
Raynal-Olive et al.

(10) Patent No.: US 7,296,678 B2
(45) Date of Patent: Nov. 20, 2007

(54) PACKAGING FOR THE TRANSPORT OF STERILE OBJECTS OR OBJECTS TO BE STERILISED

(75) Inventors: Claire Raynal-Olive, Vif (FR); Jean-Pierre Grimard, Vif (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 191 days.

(21) Appl. No.: 10/511,577

(22) PCT Filed: May 6, 2003

(86) PCT No.: PCT/FR03/01407

§ 371 (c)(1),
(2), (4) Date: May 2, 2005

(87) PCT Pub. No.: WO03/094999

PCT Pub. Date: Nov. 20, 2003

(65) Prior Publication Data

US 2005/0224382 A1    Oct. 13, 2005

(30) Foreign Application Priority Data

May 7, 2002 (FR) .................................. 02 05728

(51) Int. Cl.
*A61B 17/06* (2006.01)
*A61L 2/20* (2006.01)
*B65B 55/02* (2006.01)

(52) U.S. Cl. ................. 206/439; 206/370; 422/26; 422/300; 53/425

(58) Field of Classification Search ........ 206/438–439, 206/363–370, 570–572; 34/284–301; 422/26–28, 422/292–300; 53/396, 425
See application file for complete search history.

(56) References Cited

U.S. PATENT DOCUMENTS

| 4,055,672 | A | * | 10/1977 | Hirsch et al. ............... 206/439 |
| 6,164,044 | A | * | 12/2000 | Porfano et al. ............... 422/28 |
| 6,412,639 | B1 | * | 7/2002 | Hickey ....................... 206/438 |
| 6,566,144 | B1 | * | 5/2003 | Madril et al. ............... 436/177 |
| 6,629,602 | B1 | * | 10/2003 | Heyman ..................... 206/438 |
| 6,722,054 | B2 | * | 4/2004 | Yarborough et al. ......... 34/284 |
| 7,100,768 | B2 | * | 9/2006 | Grimard et al. ............. 206/438 |
| 2005/0226763 | A1 | * | 10/2005 | Raynal-Olive et al. ....... 422/28 |
| 2006/0054523 | A1 | * | 3/2006 | Porret et al. ................ 206/439 |

* cited by examiner

*Primary Examiner*—Bryon P. Gehman
(74) *Attorney, Agent, or Firm*—David M. Fortunato; Cohen Pontani Lieberman & Pavane LLP

(57) ABSTRACT

A packaging having a box, and a cover sheet made of a material that is not permeable to decontamination gas. The cover sheet has a window closed by a piece of selectively impervious material. A flexible piece of a material that is not permeable to a decontamination gas is fixed to the cover sheet by at least one of its edges and has a free part which is able to move between a diffusion position and a non-diffusion position.

19 Claims, 2 Drawing Sheets

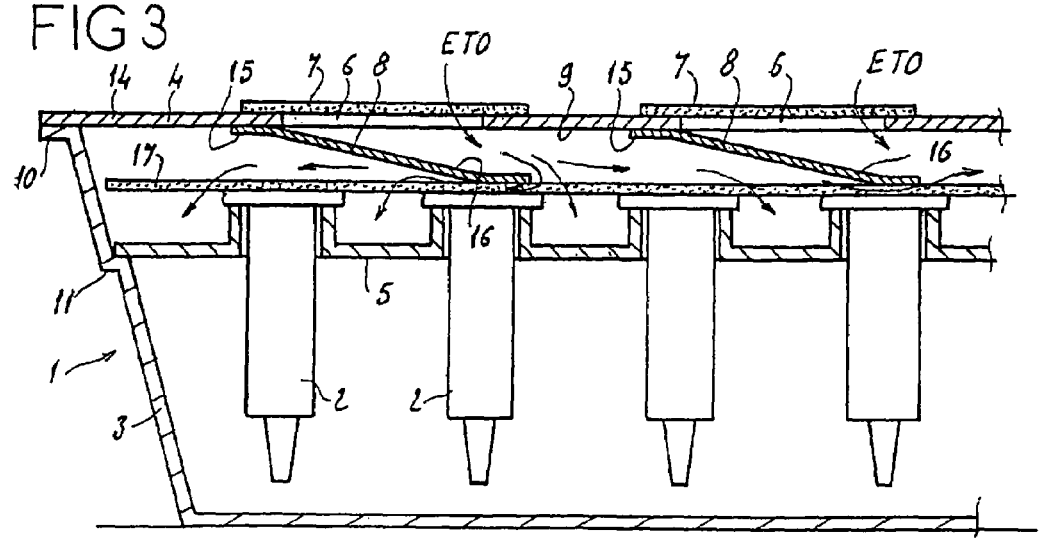
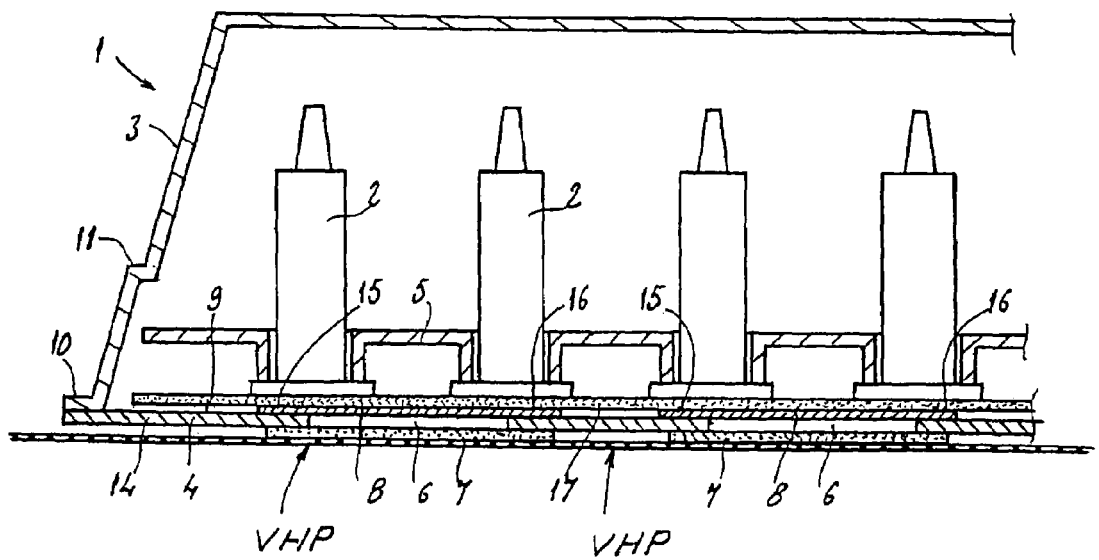

PACKAGING FOR THE TRANSPORT OF STERILE OBJECTS OR OBJECTS TO BE STERILISED

The present invention relates to a packaging intended to be used for transporting sterile objects or objects that are to be sterilized, to a method of manufacturing this packaging, and to the use of this packaging in a decontamination method. The packaging according to the invention may in particular be used for transporting syringe components, particularly syringe bodies intended to be filled later with an active product or medicinal product.

The conditions of sterility in which certain stages of the handling or transportation of objects intended for medical use are to take place are very strict, particularly in the pharmaceutical industry. It is therefore extremely important to produce packagings which are compatible with such requirements.

In the remainder of the description, mention will be made of a selectively impervious material which ought to be defined. The expression "selectively impervious" as used in this description and in the claims is to be understood as meaning that the material is designed, in terms of structure, to control any exchange between the inside of the packaging and its external environment. This means, among other things, that the packaging is impervious, individually or in combination, to contamination by microorganisms, bacteria and/or biologically active material likely to come into contact with the packaging while it is being handled, while at the same time remaining permeable to gases in general. The degree of permeability to gases can vary according to the nature of the gas. As a preference, the selectively impervious material will allow easy passage of a sterilization gas, such as ethylene oxide (ETO) for example, and will limit the passage of a decontamination gas, such as hydrogen peroxide vapors for example.

It is known practice for sterile objects or objects that are to be sterilized to be placed in a box made of plastic, and then for a cover sheet made of a selectively impervious material to be fixed to this box so as to seal it, for the box thus sealed to be placed in a second packaging comprising a window closed by a sheet of selectively impervious material, and for the whole thing to be sterilized using a gas of the ETO type. The packaging thus sterilized is placed in a cardboard box for dispatch; on reaching its destination, the cardboard box and said second packaging are opened, then said plastic box is decontaminated and opened.

In the case of syringe components, it is known practice for use to be made of a box made particularly of polystyrene and of a cover sheet made of a material marketed under the tradename TYVEK®, sealed to the box. This material is formed on the basis of filaments of HDPE (high density polyethylene) or some other polymer, bound in particular by heat and pressure.

For said second packaging, it is known practice for use to be made of a plastic bag, the closure sheet for the window that this bag has also being made of "TYVEK®".

At its destination, after this second packaging has been removed, the box is exposed to decontamination gas, for example to hydrogen peroxide vapors, so as to decontaminate it. This exposure takes place in an airlock or tunnel conveying this box to a sterile zone.

This type of decontamination is well suited to certain uses, particularly to the decontamination of packagings containing syringe bodies like the aforementioned. However, the applicant has observed that in certain!cases, there were undesirable interactions between the objects contained in the packaging, particularly the syringe bodies, and the products with which these objects then come into contact, particularly active products or medicinal products used later to fill the syringe bodies. This phenomenon seemed to exist more especially when "TYVEK®" was used as the selectively impervious material.

The invention aims to overcome this significant drawback. Its objective is therefore to provide a packaging for sterile objects or objects that are to be sterilized, that can be decontaminated using a decontamination gas, for example, using hydrogen peroxide vapors without there subsequently being undesirable interactions between the objects contained in the packaging, particularly syringe bodies, and products with which these objects are intended to come into contact later, particularly active products or medicinal products which will later fill the syringe bodies.

The objective of the present invention is also to provide a method for producing this packaging.

The packaging concerned comprises, in a way known per se, a box intended to house the sterile objects or objects that are to be sterilized, and a cover sheet fixed to the box in such a way as to seal the latter imperviously.

According to the invention, said cover sheet is made of a material that is not permeable to a decontamination gas, for example to hydrogen peroxide vapors, and comprises at least one window closed by a piece of selectively impervious material, and the packaging further comprises at least one flexible piece of a material that is not permeable to a decontamination gas, for example to hydrogen peroxide vapors, the said flexible piece being fixed to the cover sheet by at least one of its edges and comprising a free part, the free part of said piece being able to move between a diffusion position, allowing unrestricted diffusion of sterilization gas into the box through the window, and a non-diffusion position minimizing or even preventing the diffusion of decontamination gas, for example of hydrogen peroxide vapors, into the box through the window.

The method for manufacturing the packaging according to the invention comprises the steps consisting in:
 forming a cover sheet made of a material that is not permeable to a decontamination gas, for example to hydrogen peroxide vapors, while forming at least one window in this cover sheet;
 placing a piece of a selectively impervious material in said window in such a way as to close this window using this material,
 fixing a flexible piece of a material that is not permeable to a decontamination gas, for example to hydrogen peroxide vapors, over the cover sheet, said flexible piece being fixed to the cover sheet by at least one of its edges and comprising a free part, said free part being positioned facing the window,
 placing the objects that are to be packaged in a box, and
 fixing said cover sheet over the box in such a way as to seal this box imperviously.

The invention also relates to the use of the aforementioned packaging in a method for decontaminating this packaging using a decontamination gas, for example using hydrogen peroxide vapors.

The invention also relates to a sterilization and decontamination method using the above packaging, characterized in that it comprises the steps consisting in:
 placing the packaging in a diffusion position during the sterilization process; and
 placing the packaging in a non-diffusion position during the decontamination process.

What the applicant actually observed was that hydrogen peroxide residues remained on the objects contained in the box when the selectively impervious material was not impervious to hydrogen peroxide vapors, as proved to be the case with "TYVEK®", and that these residues were the cause of the aforementioned undesirable interactions. These interactions occurred especially in the case of syringe bodies, said residues building up therein because of the fact that hydrogen peroxide vapors are heavier than the air contained in the packaging.

The invention solves this problem by providing a cover sheet made of a material not permeable to a decontamination gas, for example to hydrogen peroxide vapors, which allows the objects contained in the box to be protected efficiently against this decontamination gas, for example against hydrogen peroxide vapors, but which has at least one window closed by a piece of selectively impervious material so as to allow the sterilization gases to enter this box, a flexible piece of a material that is not permeable- to a decontamination gas, for example to hydrogen peroxide vapors, being fixed to the cover sheet by at least one of its edges, facing the window. Thanks to its free part and to its flexibility, the flexible piece acts as valve. Thus, in the diffusion position, the free part of this flexible piece, on account of gravity, is detached from the cover sheet. As a result, it does not cover the window facing which it is fixed and leaves this window free for the passage of sterilization gas through this window to the inside of the box and the objects that are to be sterilized. By contrast, in a non-diffusion position, for example when the packaging has been placed in an inverted position with respect to the diffusion position, the free part of the flexible piece covers the window and minimizes or even prevents the passage of decontamination gas through this window.

The cover sheet is made of a material that is not permeable to a decontamination gas, for example to hydrogen peroxide vapors. A "material that is not permeable to a decontamination gas" is to be understood, in the meaning of this invention, to be a material that minimizes or even prevents the diffusion of a decontamination gas, for example hydrogen peroxide vapors, through this material. As a preference, this material is chosen from flexible or nonflexible polymers, polyolefins such as polyethylene or polypropylene, polyester, polyamide and combinations thereof.

As a preference, the piece of selectively impervious material is made of porous material. As a preference, this selectively impervious material is chosen from paper, materials based on natural fibers, for example plant fibers or synthetic fibers, materials based on filaments of high density polyethylene, or some other polymer, these being bound in particular by heat and pressure, and combinations thereof. As a further preference, the selectively impervious material is a material based on high density polyethylene bound by heat and pressure, particularly the material marketed under the tradename TYVEK® by DuPont de Nemours.

The flexible piece may be fixed to the cover sheet for example by bonding or welding.

In one embodiment of the invention, the box has a rim protruding beyond the cover sheet and the flexible piece is fixed to the exterior face of the cover sheet.

In another embodiment of the invention, the flexible piece is fixed to the interior face of the cover sheet.

Advantageously, the flexible piece is fixed to the cover sheet facing the window. As a preference, the flexible piece has a shape similar to that of the window, the area of the flexible piece being greater than that of the window so that in the non-diffusion position, the flexible piece covers this window with an overlap around its entire perimeter.

In a preferred embodiment of the invention, the cover sheet comprises several windows each closed by a piece of selectively impervious material. In this case, the flexible piece may be fixed to the cover sheet facing several windows, so that in the non-diffusion position, the flexible piece covers, with overlap, all of these windows.

Alternatively, several flexible pieces may be fixed to the cover sheet, one facing each window, so that in the non-diffusion position, each flexible piece, covers, with overlap, the window facing which it is fixed.

The flexible piece is made of a material not permeable to a decontamination gas, for example to hydrogen peroxide vapors. As a preference, this material is chosen from flexible or non-flexible polymers, polyolefins, such as polyethylene or polypropylene, polyester, polyamide and combinations thereof.

A box of the packaging according to the invention is preferably made of a rigid or semirigid plastic. As a preference, this material is chosen from polystyrene, polypropylene, polycarbonate, polyester, polyvinylchloride and combinations thereof.

The packaging may also comprise, inside the box, at least one layer limiting the passage of a decontamination gas, for example hydrogen peroxide vapors, or able to absorb a decontamination gas, for example hydrogen peroxide vapors.

These layers thus make it possible to limit the introduction of these hydrogen peroxide vapors into the box or to absorb the hydrogen peroxide vapors that may have managed to enter this box.

This layer may have a shape and size such that it can be placed along the cover sheet and that it extends, in this position, between the cover sheet and the objects contained in the packaging.

When the flexible piece is fixed to the exterior face of the cover sheet, said layer or at least one of said layers may be attached to the cover sheet particularly by bonding or welding; this or these layers are then sized in such a way as to delimit on the cover sheet a peripheral region for fixing this cover sheet to the box.

Said layer or at least one of said layers may also simply be placed over the objects placed inside the box, prior to the sealing of the cover sheet, or on supports provided for that purpose, or on an objects-positioning piece placed in this box.

When the flexible piece is fixed to the exterior face of the cover sheet, the packaging may also comprise at least one of said layers attached to the cover sheet and at least one other of said layers arranged inside the box.

Said layer may be a material based on filaments of high density polyethylene, or some other polymer, bound in particular by heat and pressure, and in particular the material marketed under the tradename TYVEK®.

Said layer may also be made of a material based on natural fibers, for example plant fibers, or comprise a metallized or metallic sheet, a plastic or comprise at least two complementing sheets made of selectively impervious material.

The invention will be better understood with the aid of the attached drawing in which:

FIG. 3 is a part view in longitudinal section according to a second embodiment in a position in which the packaging is placed during said sterilization process, the cover sheet comprising two windows, FIG. 4 is a view similar to FIG. 3, in an inverted position with respect to FIG. 3, in which position the packaging is placed during said decontamination process.

For simplicity, the parts or elements of the first embodiment that are used identically or similarly in the second embodiment will be denoted by the same numerical references and will not be described again in detail.

Figure 1:
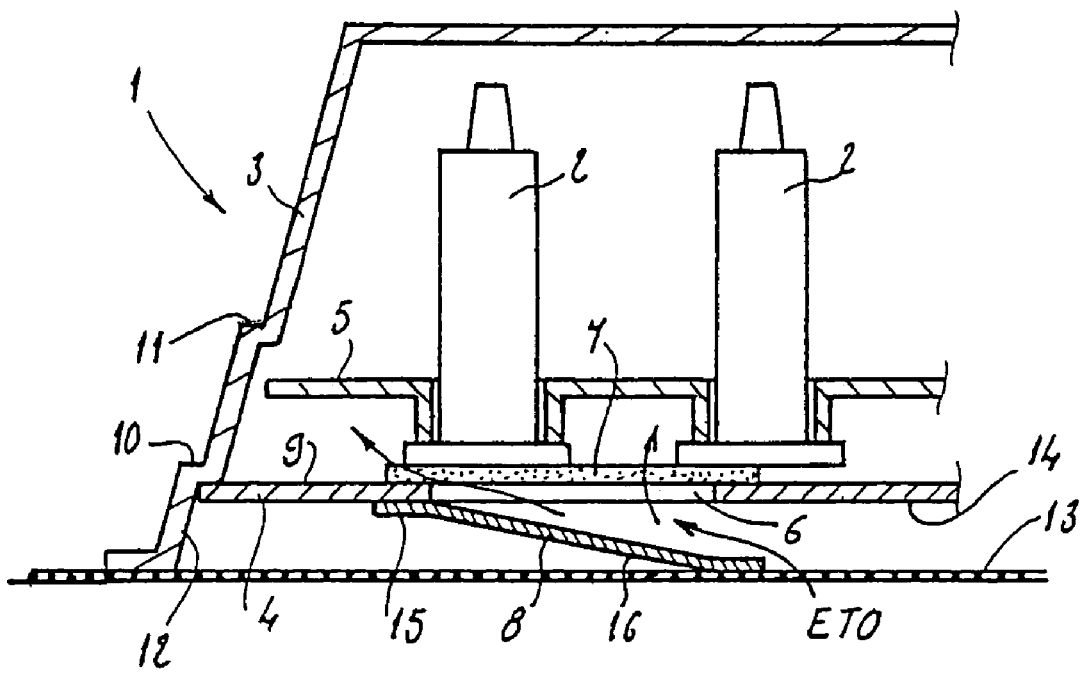
FIG. 1 is a part view in longitudinal section according to a first embodiment, in a position in which the packaging is placed during the sterilization process using a sterilization gas, for example ethylene oxide (ETO)
Figure 2:
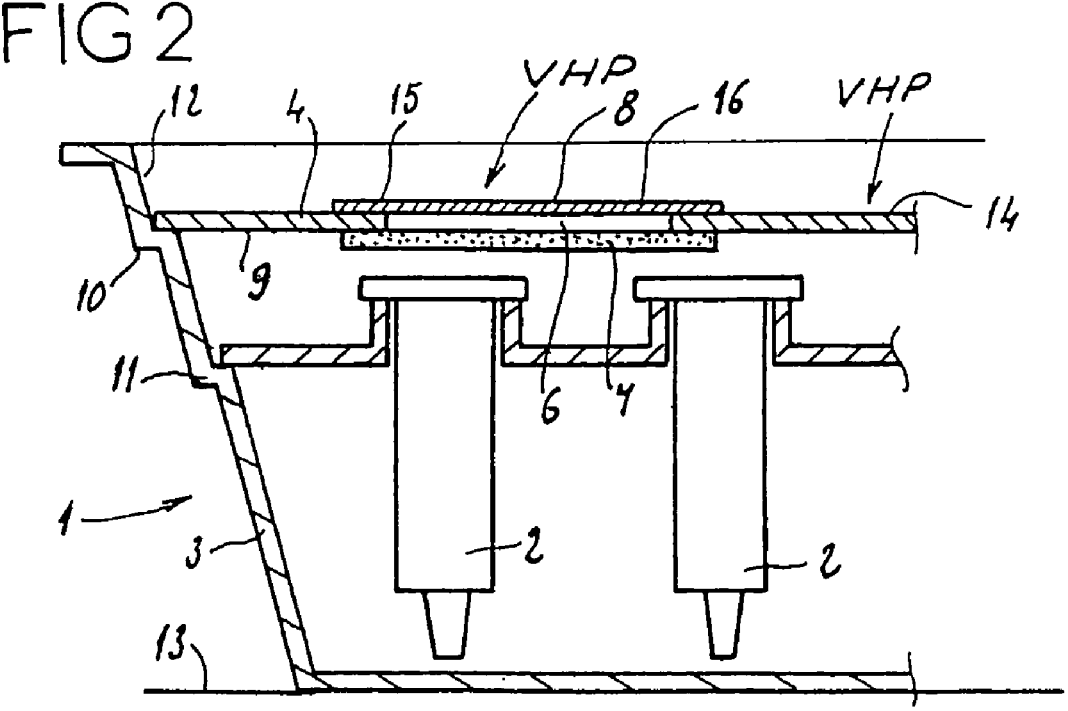
FIG. 2 is a view similar to FIG. 1, in an inverted position with respect to FIG. 1, in which position the packaging is placed during the subsequent decontamination process using a decontamination gas, for example hydrogen peroxide vapor (VHP)

FIGS. 1 and 2 depict a packaging 1 used for transporting syringe components, in particular, in the example depicted, syringe bodies 2, intended to be filled later with an active produce or a medicinal product.

The packaging 1 comprises a box 3, a plate 5 supporting the syringe bodies 2 and a cover sheet 4 fixed to the box 3 in such a way as to seal the latter imperviously.

The box 3 is made of polystyrene and has a peripheral flange 10 for the sealing of the sheet 4. It also forms a shoulder 11 to house the plate 5. The box 3 also comprises a rim 12 protruding beyond the cover sheet 4. In FIG. 1, the box 3 rests on a discontinuous support, in this instance a grating 13, in a position in which the syringe bodies 2 are in a neck down position.

The cover sheet 4 is made of a material not permeable to a decontamination gas, and has a window 6 closed by a piece 7 made of "Tyvek®", which is a selectively impervious material. This piece 7 is welded to the interior face 9 of the cover sheet 4. Facing the window 6, a flexible piece 8 is fixed to the exterior face 14 of the cover sheet 4. This flexible piece 8 is welded to the cover sheet 4 via one of its edges 15 and has a free part 16. Because of the presence of the rim 12, because of the flexibility of the piece 8 and because of gravity, the free part 16 rests on the grating 3 on which the packaging 1 is placed.

Thus, in this diffusion position depicted in FIG. 1, the sterilization step is performed. The sterilization gas, embodied by ETO and the corresponding arrows in FIG. 1, diffuses through the grating 13 then through the window 6 and the piece 7 of selectively impervious material toward the inside of the box 3, thus bathing the syringe bodies 2 that are to be sterilized.

FIG. 2 depicts the non-diffusion position. The packaging is in an inverted position by comparison with the position in FIG. 1. Because of the flexibility of the flexible piece 8 and because of gravity, the free part 16 of this flexible piece 8 entirely covers the window 6 closed by the piece 7 of selectively impervious material. In this position, the flexible piece 8 minimizes or even prevents the diffusion of decontamination gas, that is to say of hydrogen peroxide vapors embodied by VHP and the corresponding arrows in FIG. 2.

In the second embodiment shown in FIGS. 3 and 4, the box 3 has no rim protruding beyond the cover sheet 4 and the cover sheet 4 has two windows 6 each closed by a piece 7 of selectively impervious material welded to the exterior face 14 of the cover sheet 4. Facing each window 6, a flexible piece 8 is welded, via one of its edges 15, to the interior face 9 of the cover sheet 4.

The packaging 1 also comprises a layer 17 of Tyvek®, which is a selectively impervious material. This layer 17 is positioned between the syringe bodies 2 and the cover sheet 4.

In the diffusion position depicted in FIG. 3, because of the flexibility of the flexible piece 8 and because of gravity, the free part 16 of the flexible piece 8 rests on the layer 17 of selectively impervious material and allows free passage to the sterilization gas through the window 6.

In this position, the packaging is sterilized using the sterilization gas, in this instance ethylene oxide embodied by ETO and the corresponding arrows in FIG. 3. The ethylene oxide diffuses into the box 3 through the windows 6 and the layer 17 of selectively impervious material and bathes the syringe bodies 2 that are to be sterilized.

FIG. 4 depicts the non-diffusion position. The packaging is in an inverted position with respect to the position of FIG. 3. For each window 6, because of the flexibility of the flexible piece 8 and because of gravity of the entity consisting of the plate 5, the syringe bodies 2 and the layer 17, the free part 16 of the flexible piece 8 entirely covers the window 6 closed by the piece 7 of selectively impervious material. In this position, the flexible pieces 8 minimize or even prevent the diffusion of the decontamination gas, that is to say of the hydrogen peroxide vapors embodied by VHP and the corresponding arrows in FIG. 4.

The invention provides a marked improvement to the prior art by supplying a packaging that is effective with regard to possible ingress of decontamination gas, for example hydrogen peroxide vapors, during the decontamination process without significantly weakening the ability of this package to be sterilized by means of a sterilization gas. The invention also provides an improved method for sterilizing and decontaminating this packaging.

The invention is not restricted to the embodiments described hereinabove by way of examples.

The invention claimed is:

1. A packaging intended to be used for transporting sterile objects or objects that are to be sterilized, comprising a box intended to house the objects; a cover sheet fixed to the box in such a way as to seal the box imperviously, said cover sheet being made of a material that is not permeable to a decontamination gas and which comprises a window closed by a piece of selectively impervious material, and having a flexible piece of a material that is not permeable to a decontamination gas, said flexible piece being fixed to the cover sheet by at least one of its edges and comprising a free part being able to move between a diffusion position, allowing unrestricted diffusion of sterilization gas into the box through the window, and a non-diffusion position to prevent at least a portion of the decontamination gas from entering the box through the window.

2. The packaging as claimed in claim 1, wherein the selectively impervious material is chosen from paper, materials based on natural fibers, materials based on synthetic fibers, materials based on filaments of high density polyethylene, or and materials based on polymer bound by heat and pressure.

3. The packaging as claimed in claim 2, wherein the selectively impervious material is a material based on filaments of high density polyethylene bound by heat and pressure.

4. The packaging as claimed in claim 1, wherein the box has a rim extending beyond the cover sheet, and the flexible piece is fixed to the exterior face of the cover sheet.

5. The packaging as claimed in claim 1, wherein the flexible piece is fixed to an interior face of the cover sheet.

6. The packaging as claimed in claim 1, wherein the flexible piece is fixed to the cover sheet facing the window.

7. The packaging as claimed in claim 1, wherein the flexible piece has a shape similar to the shape of the window, the area of the flexible piece being greater than that of the window so that in the non-diffusion position, the flexible piece covers the window with overlap around the entire periphery of the window.

8. The packaging as claimed in claim 1, wherein the cover sheet has several windows each closed by a piece of selectively impervious material.

9. The packaging as claimed in claim 8, wherein the flexible piece is fixed to the cover sheet facing the several windows so that in the non-diffusion position, the flexible piece covers the several windows with overlap.

10. The packaging as claimed in claim 8, wherein several flexible pieces are fixed to the cover sheet, with each flexible piece facing a corresponding one of the several windows so that in the non-diffusion position, each flexible piece covers, with an overlap its corresponding windows.

11. The packaging as claimed in claim 1, wherein the packaging comprises, inside the box, at least one layer capable of one of limiting the passage of a decontamination gas and absorbing decontamination gas.

12. The packaging as claimed in claim 11, wherein the said layer has shape and size such that it can be placed along the cover sheet and that, in this position, the layer extends between the cover sheet and the objects contained in the packaging.

13. The packaging as claimed in claim 11, wherein said layer is arranged over the objects placed inside the box prior to the cover sheet being sealed.

14. A method of manufacturing the packaging as claimed in claim 1, comprising the steps of: forming the cover sheet made of a material that is not permeable to a decontamination gas; forming the window in the cover sheet; placing the piece of a selectively impervious material in said window in such a way as to close the window using the material; fixing the flexible piece of a material that is not permeable to decontamination gas, said flexible piece of the material that is not permeable to decontamination gas being fixed to the cover sheet by at least one of its edges and comprising a free part positioned facing the window, placing the objects that are to be packaged in a the box; and fixing said cover sheet over the box in such a way as to seal the box imperviously.

15. The method as claimed in claim 14, wherein the flexible piece is fixed to an exterior face of the cover sheet.

16. The method as claimed in claim 14, wherein the flexible piece is fixed to an interior face of the cover sheet.

17. A use of the packaging as claimed in claim 1 in a method for decontaminating the packaging using a decontamination gas.

18. A use of the packaging as claimed in claim 1 for transporting syringe components, which are intended to be filled after transport with one of an active product and a medicinal product.

19. A sterilization and decontamination method using a packaging as claimed in claim 1, comprising the steps of: placing the packaging in a diffusion position during the sterilization process; and placing the packaging in a non-diffusion position during the decontamination process.

* * * * *